United States Patent [19]

Ezekiel

[11] 4,009,176
[45] Feb. 22, 1977

[54] CONVERSION OF 2-AMINONAPHTHO [1,2-d] SELENAZOLE TO 2-METHYLNAPHTHO[1,2-d] SELENAZOLE

[75] Inventor: Aaron David Ezekiel, Ilford, England

[73] Assignee: Ciba-Geigy AG, Basel, Switzerland

[22] Filed: July 30, 1975

[21] Appl. No.: 600,483

Related U.S. Application Data

[62] Division of Ser. No. 510,945, Sept. 30, 1974, Pat. No. 3,969,364.

[30] Foreign Application Priority Data

Oct. 19, 1973   United Kingdom ............ 48778/73
Oct. 19, 1973   United Kingdom ............ 48779/73

[52] U.S. Cl. .............................................. 260/298
[51] Int. Cl.² ..................................... C07D 293/12
[58] Field of Search ................................... 260/298

[56] References Cited

UNITED STATES PATENTS 2,330,791   9/1943   Middleton et al. ................ 260/298
3,102,142   8/1963   Horwitz et al. .................... 260/578

*Primary Examiner*—Donald G. Daus
*Assistant Examiner*—Diana G. Rivers
*Attorney, Agent, or Firm*—Wenderoth, Lind & Ponack

[57] ABSTRACT

This invention relates to the new compound 2-aminonaphtho[1,2-d] selenazole of the formula

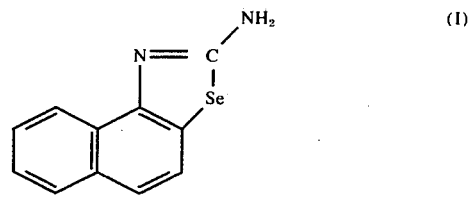

Compound (I) is prepared by halogenating 1,2,3,4-tetrahydro-1-oxonaphthalene-3-sulphonate, reacting the halogenated compound with selenourea and then eliminating the sulphonic acid group. Compound (I) is useful as starting material for the preparation of 2-methylnaphtho [1,2-d] selenazole by hydrolyzing compound (I), acylating the hydrolysis product and ring closure.

2 Claims, No Drawings

CONVERSION OF 2-AMINONAPHTHO[1,2 d] SELENAZOLE TO 2-METHYLNAPHTHO[1,2 d] SELENAZOLE

This is a divisional application of application Ser. No. 510,945, filed Sept. 30, 1974, now U.S. Pat. No. 3,969,364.

Subject of the present invention is the novel compound 2-aminonaphtho [1,2-d] selenazole which has the formula

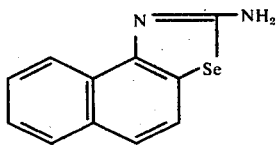

According to the present invention 2-aminonaphtho [1,2-d] selenazole is prepared by halogenating an aqueous acetic acid solution of a 1, 2, 3, 4-tetrahydro-1-oxonaphthalene-3-sulphonate or -sulphonic acid of the formula

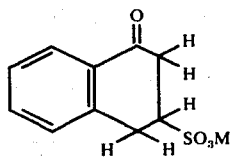

wherein M is an alkali metal or a hydrogen atom by treatment with chlorine or bromine at a temperature of 20° to 100° C, increasing the pH of the reaction mixture to within the range of 5.0 to 9.5 and then reacting the halogenated compound with an aqueous solution of selenourea at a temperature of 20° to 100° C, to produce a compound of the formula

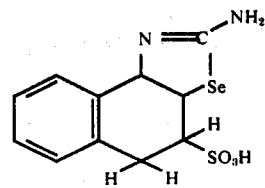

and then eliminating the sulphonic acid group by base catalysis.

Preferably the base used to eliminate the sulphonic acid group is sodium hydroxide or potassium hydroxide.

The preferred halogenating agent is bromine.

The ring closing step using selenourea is preferably carried out in the presence of sodium acetate and under reflux.

The process of the present invention can be represented schematically thus:

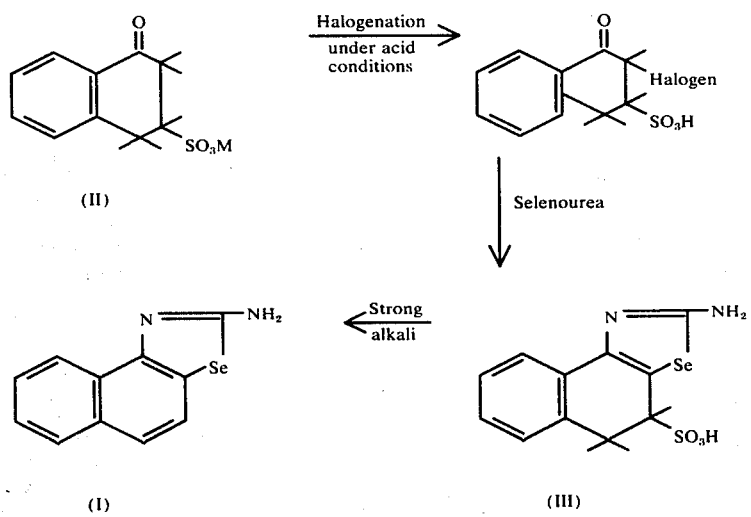

The 2-aminoaphtho [1,2-d] selenazole of the present invention is useful as an intermediate in the production of 2-methylnaphtho [1,2-d] selenazole of the formula

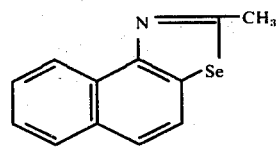

which is of particular use in the production of optical sensitising dyes. A method of preparing 2-methylnaphtho [1,2-d] selenazole is described in Example II and III of U.S. Pat. No. 2,339,094, but this method involves the use of naphthylamines and nitronaphthalenes which compounds are known to be strongly carcinogenic. However by use of the novel compound of this invention it is possible to provide a process for the production of 2-methylnaphtho [1,2-d] selenazole which does not involve the use of naphthylamines or nitronaphthalenes.

Therefore the present invention also relates to a process for the preparation of 2-methylnaphtho [1,2-d] selenazole of the formula (IV) which comprises hydrolysing 2-aminonaphtho [1,2-d] selenazole of the formula (I) in the presence of a reducing agent at a temperature of over 130° C in a high-boiling inert solvent medium and acetylating the resultant hydrolysis product in situ with acetic anhydride in the presence of acetic acid to produce a compound of the formula

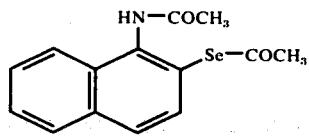
(V)

and then ring closing this compound to produce the 2-methylnaphtho [1,2-d] selanazole.

Preferably the 2-aminonaphtho [1,2-d] selenazole is hydrolysed by use of potassium hydroxide. However it maybe hydrolysed by use for example of sodium hydroxide or a mixture containing potassium hydroxide and potassium carbonate.

The preferred reducing agent in the presence of which the selenazole is hydrolysed in an alkali metal or ammonium borohydride. Other suitable reducing agents are, for example, zinc dust and sodium dithionite.

As the hydrolysis reaction is carried out at a temperature of over 130° C it is preferred that the boiling point of the high-boiling point inert solvent medium is over 150° C and most preferably from 160°–200° C. A suitable high-boiling inert solvent medium is ethane-1, 2-diol.

Ring closure of the compound of formula V to produce 2-methylnaphtho [1,2-d] selenazole if preferably effected by refluxing the compound of formula V with acetic anhydride. However ring closure may be effected by a number of other methods known per se for example heating the compound of formula V to a temperature of about 200° C.

EXAMPLE 1

2-Amino-4,5-dihydronaphtho
[1,2-d]selenazole-4-sulphonic acid (Bromination)

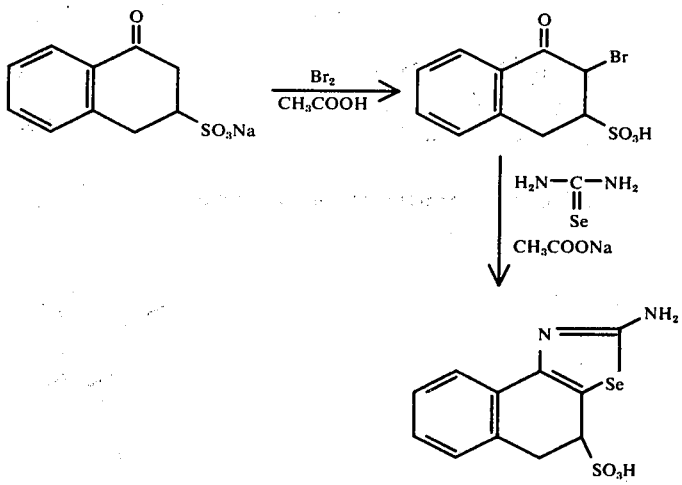

Sodium 1,2,3,4-tetrahydro-1-oxonaphthalene-3-sulphonate, produced by the method of S. V. Bogdanov and N. N. Karandasheva, Zhurnal Obshchei Khimii, 1956, 26, 3365–3368 [Chem.Abstr.1957,51,9544[b]], (245 g) was suspended in 95% acetic acid (2 liters) and the suspension was warmed on a water-bath (65°C) whereupon a clear solution was obtained. To the stirred solution, maintained at this temperature, bromine (154 g) in acetic acid (300ml) was added dropwise over a period of 1 hour. The mixture was stirred for an additional period of 1 hour and the solvent was then evaporated under reduced pressure (bath temperature 50° C. The last traces of acetic acid were eliminated by dissolving the syrup in water (500ml) and evaporating the aqueous solution under reduced pressure to dryness.

This process was repeated twice. The syrup was then dissolved in water (600 ml) and the solution was stirred and cautiously neutralised with aqueous sodium hydrogen carbonate to pH 5.0. The neutral solution (1350 ml) of the bromo compound was stirred and treated with sodium acetate (40 g) in water (100ml) and the solution was heated under reflux. A solution of selenourea (133 g) in hot water (750 ml) was added to the stirred bromocompound and the mixture was heated under reflux for 1 hour after the addition of the selenourea. The reddish brown solid was collected, washed well with water, then with methanol, acetone and finally ether. After drying at 60° C the 2-amino-4,5-dihydronaphtho [1,2-d] selenazole-4-sulphonic acid weighed 223 g and contained black selenium.

2-Aminonaphtho [1,2-d] selenazole

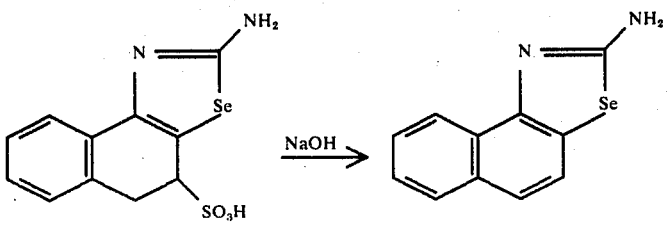

The foregoing sulphonic acid (223 g) was dissolved in 2M sodium hydroxide (1,35 liters), filtered free from selenium, washed with water (1 liter) and the combined filtrate was heated on a steam-bath for 1 hour whereupon a crystalline product separated. The 2-aminonaphtho-[1,2-d] selenazole filtered from the warm solution, washed well with water and dried at 60°.

| M.P. | 179–181° C |
|---|---|
| Yield | 81.7 g |
| Found: | 53,2C, 3.4H, 11.5N. |
| $C_{11}H_8N_2Se$ requires | 53.5C, 3.3H, 11.3%N. |

$\mu$ max$^{KBr}$ 3250 cm$^{-1}$ (NH$_2$); 785 & 750 cm$^{-1}$ (phenyl).

Example 2

2-Amino-4,5-dihydronaphtho-[1,2-d]-selenazole-4-sulphonic acid (Chlorination)

Sodium 1.2.3.4-tetrahydro-1-oxonaphthalene-3-sulphonate (30 g) was dissolved in 95% acetic acid (300 ml) at 60° C and the clear solution was cooled to 40° C. Chlorine gas was bubbled cautiously through the stirred solution for short periods (2 minutes). When the greenish yellow colour was discharged more chlorine was bubbled through the solution and the procedure was repeated until the greenish yellow colour persisted for a period of 0.5 hr after the final addition of chlorine. In order to establish that the halogenation was complete, a drop of bromine (0.1 ml) was added to the clear solution which turned golden yellow in colour. The acetic acid was evaporated under reduced pressure and below 50° C to dryness and the resulting syrup was treated with water (100 ml). The aqueous solution was evaporated under reduced pressure to dryness in order to eliminate the last traces of acetic acid. This process was repeated twice and finally the semi-solid was dissolved in water (250 ml) and the clear solution was cautiously neutralised with saturated aqueous sodium hydrogen carbonate to pH 5.5.

The resulting solution (300 ml) was treated with anhydrous sodium acetate (5.1 g) and selenourea (34 g) and the mixture was stirred and heated under reflux for 1 hr. The crude 2-amino-4,5-dihydronaphtho [1,2-d] selenazole derivative was filtered off, washed with water then with industrial methylated spirit (3 × 50 ml). The solid was triturated for 0.5 hr with industrial methylated spirit (100 ml), filtered, washed with ether and dried. The crude product weighed 13.5 g.

For purifying the crude solid the following procedure was adopted. The solid was triturated with water (300 ml), treated dropwise with ammonia until a solution was obtained (pH 9.5) containing some suspended black selenium. The selenium was filtered off, washed with water (50 ml) and the clear pale straw coloured filtrate was cautiously acidified with acetic acid. The 2-amino-4,5-dihydronaphtho-[1,2-d]-selenazole-4-sulphonic acid precipitated as a colourless solid, which was filtered off, washed with water (3 × 50 ml), then with ethanol (50 ml) and finally with ether (50 ml). The solid was dried to a constant weight. Yield 11.9 g, m.p. 252°(d) softened at 247°–248° C.

| Found: | 39.7 C, 2.9 H, 8.2N. |
|---|---|
| $C_{11}H_{10}N_2O_3SSe$ requires: | 40.1 C, 3.1 H, 8.5% N. |
| $\mu$ may $^{KBr}$ 3300 cm$^{-1}$ ( NH$_2$) | 1200 cm$^{-1}$ (SO$_3$H) 800 cm$^{-1}$ & 740 cm$^{-1}$ (phenyl). |

Proton magnetic resonance date: Solvent D$_2$O + NaOD (1 mole equivalent)

Internal Standard Hexamethyldisiloxane.

$\delta$ 3.48 (singlet, 1H, 5H)
$\delta$ 3.60 (singlet, 1H, 5$^1$H)
$\delta$ 4.42 (doublet, 1H, 4H)
$\delta$ 7.30 – $\delta$ 8.00 (multiplet, 4H, aromatic protons).

2-Aminonaphtho-[1,2-d]-selenazole

The foregoing dihydrosulphonic acid derivative (11.0 g) was dissolved in 2M sodium hydroxide solution (66 ml). Water (84 ml) was added to the clear solution which was heated on a steam-bath for 1 hr. The 2-aminonaphtho-[1,2-d]selenazole preciptated as a colourless solid which was filtered off, washed with water and dried. Yield 5.4 g, m.p. 169° C. Recrystallisation from a mixture of ethanol/water (1:2, 150 ml) afforded colourless needles. m.p. 174°–175° C.

Found: 53.33 C, 3.17 H, 11.06 N. $C_{11}H_8N_2Se$ requires: 53.46 C, 3.26 H, 11.33% N.

Proton magnetic reasonance data. Solvent CF$_3$COOH. Internal standard Tetramethylsilane. Hydrogen count 8.

$\delta$ 7.40 – $\delta$ 8.00 (multiplet, 6H, aromatic protons)
$\delta$ 8.20 (broad singlet, 2H, NH$_2$, exchangeable protons when the spectrum was recorded in a solution of CF$_3$COOD).

EXAMPLE 3 (Use Example)

Preparation of 1-Acetamidonaphthalene-2-selenoacetate

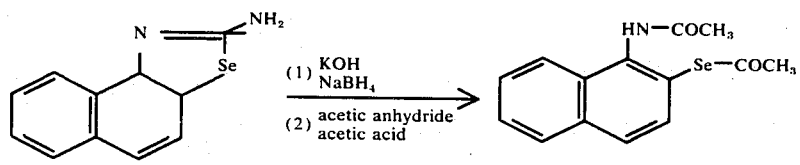

Sodium borohydride (2 g) was added to a solution of potassium hydroxide (37.5 g) in water (25 ml) and ethane-1,2-diol (100 ml) contained in a 3-necked flask equipped with a mechanical stirrer and a reflux condenser.

The air in the flask was displaced with nitrogen and 2-aminonaphtho[1,2-d] selenazole (30 g) was added to the stirred alkaline solution. Whilst meintaining a slight positive flow of nitrogen, the mixture was heated under reflux for 2 hours at a temperature of 135° C. A pale orange coloured solution was obtained which was treated with water (400 ml) containing a trace of potassium hydroxide (0.5 g) and sodium borohydride (0.2 g). The stirred solution was cooled to 10° C and acetylated cautiously with a mixture of acetic anhydride/acetic acid (1:1), 180 ml) over a period of 0.5 hour. The solid was triturated for 0.5 hour and was collected, washed with water and dried at 50°/0.1 mm. Yield 33.7 g., m.p. 136°–143° C (d). The selenol acetate was found to decompose slowly on storage.

---
Found: 54.8C, 4.2H, 4.5%N.
$C_{14}H_{13}NO_2Se$ requires 54.9C, 4.3H, 4.7%N.
$\mu$ max$^{KBr}$ 1730 & 1710 cm$^{-1}$ (CO).

---

Proton magnetic resonance date: 60MHz. Solvent $CDl_3$.
Internal standard: Tetramethylsilane. Hydrogen count 13.

---
δ 2.34 (s, 3H, CH$_3$, SeAc)
δ 2.56 (s, 3H, CH$_3$, NAc)
δ 7.3 – δ 8.3 (m, 7H, aromatic protons + NH).
s - singlet. m - multiplet.

---

Preparation of 2-Methylnaphtho[1,2-d]selenazole

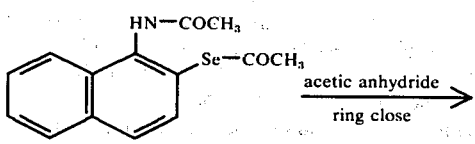 acetic anhydride ring close 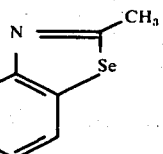

The foregoing solenol acetate (35.5 g) was dissolved in boiling acetic anhydride (400 ml). The solution was vigorously stirred and cautiously treated with zinc dust (0.5 g) in order to ensure that no diselenide is produced. The pale yellow colour was promptly discharged and to the boiling solution more zinc dust (1.5 g) was added. The mixture was heated under reflux for 0.5 hr and the zinc was filtered off and washed with acetic acid (100 ml). The combined filtrate was evaporated under reduced pressure to a low volume (80 ml). The flask was then transferred to an oil bath to distil the acetic anhydride (bath temp. 180° C. Finally the 2-methylnaphtho[1,2-d] selenazole was distilled under vacuo, b.p. 170°/0.5 mm. Yield 22 g. The solid was dissolved in boiling methanol (500 ml) and the solution was evaporated under reduced pressure to a low volume (100 ml). The crystalline solid was collected and dried under vacue. Yield 19.3 g, m.p. 109°–110° C. Concentration of the filtrate to a low volume (30 ml) afforded more solid. Yield 1.4 g, m.p. 110°.

Found: 58.4C. 3.7H, 5.6%N. $C_{12}H_9NS_e$ requires 58.3C, 3.6H, 5.7%N.

Proton magnetic resonance date: 60MHZ. Solvent: $CDCl_3$.
Internal standard: Tetramethylsilane. Hydrogen count 9.

---
δ 2.89 (s, 3H, CH$_3$)
δ 7.40 – 8.0 (m,5H, aromatic protons)
δ 8.85 (q, 1H, aromatic proton).
s - singlet. m - multiplet. q - quartet.

---

What we claim is:

1. A process for the conversion of 2-aminonaphtho[1,2-d] selenazole to 2-methylnaphtho [1,2-d] selenazole of the formula

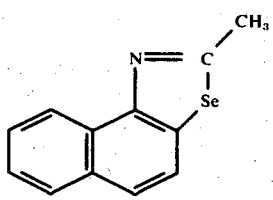

which comprises hydrolyzing with potassium hydroxide, sodium hydroxide or a mixture containing potassium hydroxide and potassium carbonate, 2-aminonaphtho [1,2-d] selenazole in the presence of an alkali metal borohydride or ammonium borohydride at a temperature of over 130° C in a high-boiling inert solvent medium and acetylating the resultant hydrolysis product in situ with acetic anhydride in the presence of acetic acid, thus producing the compound of the formula

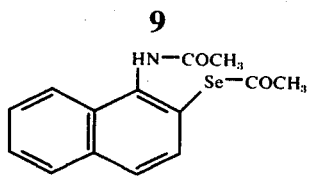
isolating this compound and closing the ring by refluxing it in the presence of acetic anhydride to form the 2-methylnaphtho [1,2-d] selenazole.
2. A process according to claim 1 wherein the high-boiling inert solvent medium is ethane - 1,2-diol.
* * * * *